(12) United States Patent
Stefinovic et al.

(10) Patent No.: US 9,730,932 B2
(45) Date of Patent: Aug. 15, 2017

(54) PHARMACEUTICAL COMPOSITION CONTAINING CRYSTALLINE MACITENTAN

(71) Applicant: SANDOZ AG, Basel (CH)

(72) Inventors: Marijan Stefinovic, Kundl (AT);
Johannes Raneburger, Kundl (AT);
Ludwig Englmeier, Holzkirchen (DE)

(73) Assignee: SANDOZ AG, Basel (CH)

( * ) Notice: Subject to any disclaimer, the term of this patent is extended or adjusted under 35 U.S.C. 154(b) by 0 days.

(21) Appl. No.: 14/781,681

(22) PCT Filed: Apr. 17, 2014

(86) PCT No.: PCT/EP2014/057883
§ 371 (c)(1),
(2) Date: Oct. 1, 2015

(87) PCT Pub. No.: WO2014/173805
PCT Pub. Date: Oct. 30, 2014

(65) Prior Publication Data
US 2016/0074398 A1 Mar. 17, 2016

(30) Foreign Application Priority Data

Apr. 22, 2013 (EP) .................................... 13164724

(51) Int. Cl.
| | | |
|---|---|---|
| *A61K 31/506* | (2006.01) | |
| *A61J 1/03* | (2006.01) | |
| *A61K 9/28* | (2006.01) | |
| *A61K 9/20* | (2006.01) | |
| *B65D 65/38* | (2006.01) | |

(52) U.S. Cl.
CPC .............. *A61K 31/506* (2013.01); *A61J 1/03* (2013.01); *A61K 9/2018* (2013.01); *A61K 9/2077* (2013.01); *A61K 9/2095* (2013.01); *B65D 65/38* (2013.01); *B65D 2565/388* (2013.01)

(58) Field of Classification Search
None
See application file for complete search history.

(56) References Cited

U.S. PATENT DOCUMENTS

| 4,721,709 A * | 1/1988 | Seth ........................ A61K 31/55 514/221 |
| 2008/0233188 A1 * | 9/2008 | Adesuyi ............... A61K 9/1652 424/465 |
| 2009/0314664 A1 * | 12/2009 | Henke ................ B65D 83/0463 206/204 |

FOREIGN PATENT DOCUMENTS

| EP | 06809280.8 | 2/2009 | |
| GB | WO 2007031933 A2 * | 3/2007 | .......... A61K 9/1652 |
| WO | 02/053557 | 7/2002 | |
| WO | 2007/031933 | 3/2007 | |

OTHER PUBLICATIONS

Caira (Crystalline polymorphism of organic compounds, Topics in Chemistry, vol. 198, Jan. 1, 1998, p. 163-208).*
Bolli, M.H., et al., The Discovery of N [5-(4-Bromophenyl)-6-[2-[(5-bromo-2-pyrimidinyl)oxy]ethoxy]-4-pyrimidinyl] N' propylsulfamide (Macitentan), an Orally Active, Potent Dual Endothelin Receptor Antagonist, J. Med. Chem. 55, 7849-61.*
Pre-Examination Processing Notice issued in Australian Patent Application No. 2014257719, Mar. 18, 2016, pp. 1-2.
Patent Examination Report No. 1 issued in Australian Patent Application No. 2014257719, May 22, 2016, pp. 1-2.
Published Application of Australian Patent Application No. 2014257719, Oct. 30, 2014, pp. 1-27.
Notice of Acceptance issued in Australian Patent Application No. 2014257719, Jun. 22, 2016, pp. 1-2.
Response and amendment filed in Australian Patent Application No. 2014257719, May 18, 2016, pp. 1-79.
Response filed in Australian Patent Application No. 2014257719, Jun. 6, 2016, pp. 1-12.
European Search Report issued in European Patent application No. 13164724.0, Sep. 24, 2013, pp. 1-7.
Response and amendments filed in European Patent application No. 14721256.7, Jun. 6, 2016, pp. 1-3.
Center for Drug Evaluation and Research, Application No. 204410Orig1s000, Sep. 19, 2013, pp. 1-14.
Supporting Information for Center for Drug Evaluation and Research, Application No. 204410Orig1s000, Sep. 19, 2013, pp. 1-30.
Note Regarding Amendments to European Patent Application No. 06809280.8, Feb. 19, 2009, pp. 1-14.
Boni et al., J.Med.Chem. Sep. 13, 2012, vol. 55, No. 17, pp. 7849-7861.
Fiedler Encyclopedia of Excipients for Pharmaceuticals, Cosmetics and Related Areas. Wissenschaftliche Verlagsgesellschaft Stuttgart, 2013.
Bauer, Frömming and Führer, "Lehrbuch der Pharmazeutischen Technologie" Wissenschaftliche Verlagsgesellschaft Stuttgart, 9. Auflage (2012).
Augsburger and Stephen, Pharmaceutical Dosage Forms: Tablets, Third Edition, vol. 2, Informa Healthcare (2008).
International Search Report and Written Opinion issued in PCTEP2014/057883, Jun. 25, 2014, pp. 1-10.
Caira, M.: "Crystalline Polymorphism of Organic Compounds" Topics in current chemistry, springer, Berlin, De, vol. 198, Jan. 1, 1998, pp. 165-166.
Response amendment filed in European Patent Application No. 0680928.8-2112, Feb. 19, 2009, pp. 1-21.

(Continued)

*Primary Examiner* — H. Sarah Park
(74) *Attorney, Agent, or Firm* — Jeffrey S. Melcher; Manelli Selter PLLC

(57) ABSTRACT

The present invention relates to an oral solid dosage form, in particular a tablet, comprising macitentan free base polymorphic form I.

22 Claims, 1 Drawing Sheet

(56) References Cited

OTHER PUBLICATIONS

Third party observation by Actelion Pharmaceutical Ltd. pursuant to Rule 114(2), EPC, filed in the corresponding European Patent Application No. 14721256.7, Jan. 17, 2017, pp. 1-16.
Sandoz AG response to the third party observation by Actelion Pharmaceutical Ltd. pursuant to Rule 114(2), EPC, filed in the corresponding European Patent Application No. 14721256/, Jan. 17, 2017, filed Feb. 8, 2016, pp. 1-2.
Mitsubishi Polyester Film, http://www.mitsubishichem-hd.co.jp/english/kaiteki_management/kaiteki, pp. 1-2, 2017.

* cited by examiner

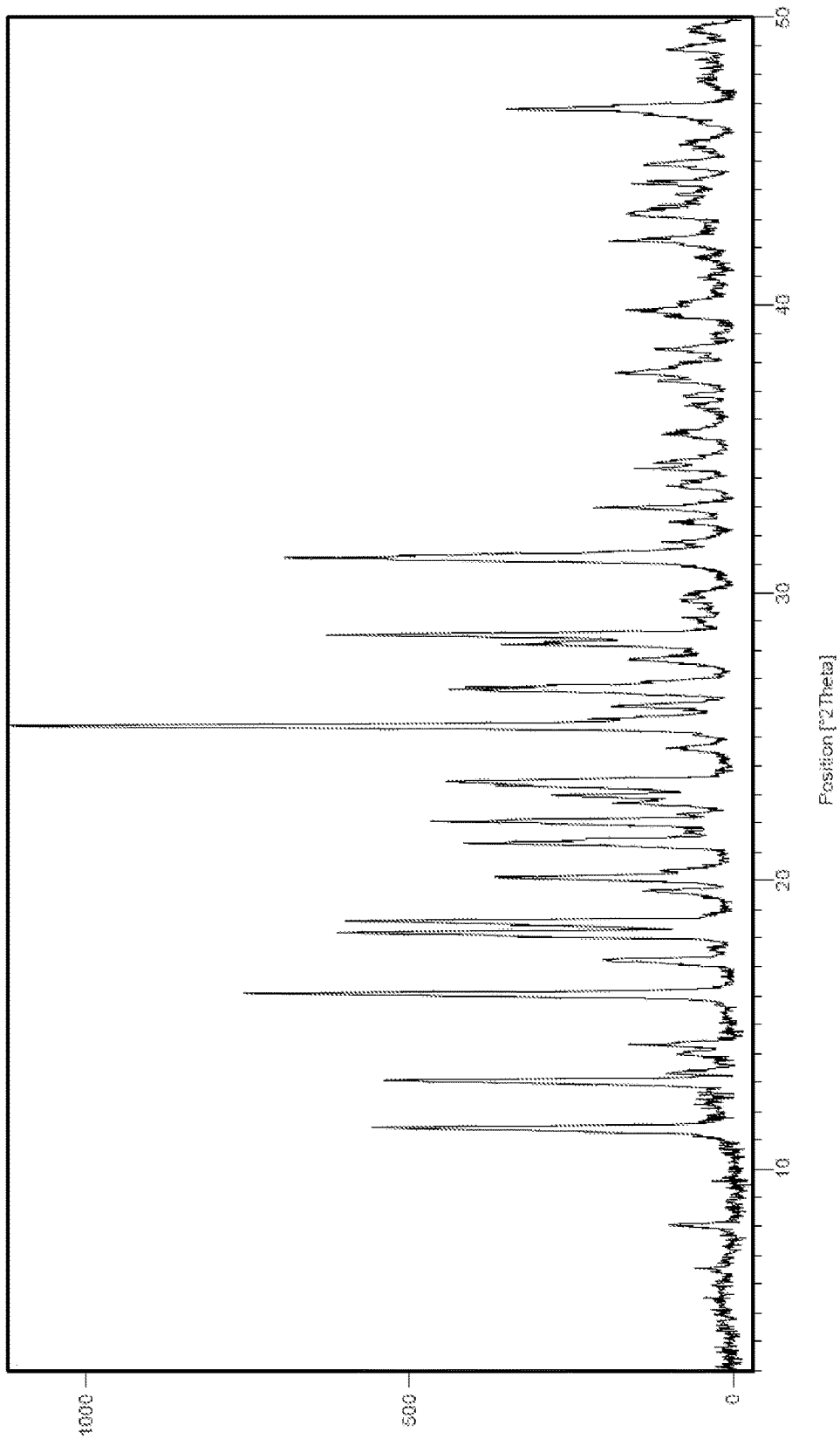

US 9,730,932 B2

PHARMACEUTICAL COMPOSITION CONTAINING CRYSTALLINE MACITENTAN

SUBJECT OF THE INVENTION

The present invention relates to a pharmaceutical composition, such as an oral solid dosage form, comprising crystalline Macitentan free base and at least one excipient. In particular, the present invention relates to an immediate release tablet comprising form I of crystalline Macitentan free base, to a method for the preparation of an oral solid dosage form, preferably of the above-mentioned oral solid dosage form, to said oral solid dosage form for use in the treatment of pulmonary arterial hypertension, and to the use of said form I of crystalline Macitentan free base for the preparation of an oral solid dosage form having increased stability.

BACKGROUND OF THE INVENTION

Macitentan, N-[5-(4-Bromophenyl)-6-[2-(5-bromopyrimidin-2-yloxy)ethoxy]pyrimidin-4-yl]-N'-propylsulfamide, of formula I

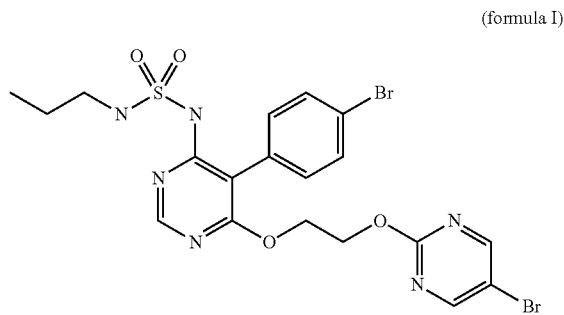 [SMILES: CCCNS(=O)(=O)Nc1ncnc(OCCOc2ncc(Br)cn2)c1-c1ccc(Br)cc1]

(formula I)

is an endothelin receptor antagonist. It is mentioned on page 134 in WO 02/53557 A1 and can be prepared by slight modification of the method described for example 104.

Macitentan is a pharmaceutically active agent which can be used for the treatment of pulmonary arterial hypertension and being tested in clinical trials for that treatment.

The preparation of closely related compounds is described in WO 02/53557 A1. In particular, example 104 describes preparation of N-[5-(4-Bromophenyl)-6-[2-(5-bromopyrimidin-2-yloxy)ethoxy]pyrimidin-4-yl]-N'-ethylsulfamide as a precipitate.

WO 2007/031933 A2 describes pharmaceutical compositions comprising Macitentan. Macitentan as obtained from WO 02/53557 is used as the starting material for the production of pharmaceutical compositions (see WO 2007/031933 A2, page 1). Preferred compositions are prepared by blending Macitentan with intra-granular materials in a high shear mixer, granulating, drying, milling, blending the milled granule with extra-granular materials except lubricant, adding lubricant and blending again, and compressing the obtained mixture into tablets. WO 2007/031933 A2 states that by using the described starting materials and the described process for manufacture, stable formulations can be produced.

In a Note regarding amendments of European patent application No. 06809280.8 of Feb. 19, 2009, it is disclosed that the preparation of stable Macitentan-containing formulations is challenging because if certain components were missing or to be replaced by others that one skilled in the art would think are equivalent, the pharmaceutical composition would have altered properties that would make it less stable and/or unsuitable for certain types of formulations (page 3 of Note). Experiments are presented which are said to show that only particular combinations of excipients are suitable for the preparation of storage stable (chemical stability was tested) pharmaceutical compositions with satisfactory dissolution properties.

Bolli et al., J. Med. Chem. 2012, 55, 7849-7861 describe synthesis of Macitentan and proceed to prepare crystalline Macitentan free base by crystallization from methanol. This is the first disclosure of crystalline Macitentan free base, and crystalline Macitentan free base is described to have a melting point of 135° C.-136° C.

The pharmaceutical compositions described in the prior art have drawbacks in that only particular excipients can be used for the preparation of storage stable pharmaceutical compositions with still satisfactory dissolution properties. Moreover, the pharmaceutical compositions described in the prior art are not yet ideal with regard to storage stability and/or dissolution properties.

OBJECT AND SUMMARY OF THE INVENTION

An object of the present invention was to find a pharmaceutical composition comprising macitentan and exhibiting improved chemical stability upon storage.

It was a further object of the present invention to find a pharmaceutical composition comprising macitentan having defined solid state characteristics for the API, in particular avoiding undesired conversion to any other solid state form taking place during the formulation process.

It was yet a further object of the present invention to find a pharmaceutical composition comprising a solid form of Macitentan, which solid form of Macitentan would allow more flexibility with regard to excipient choice and thus enable the avoidance of potentially allergic excipients or excipients which are poorly tolerated by particular patients or patient groups.

It was a further object of the present invention to find a pharmaceutical composition comprising macitentan and having improved disintegration characteristics, in particular after prolonged storage at conditions which are typical for tropical countries.

It was a further object of the present invention to find a pharmaceutical composition comprising macitentan and being suitable for storage in a packaging material with a high moisture vapour transmission rate.

These objects as well as others, which will become apparent from the following description of the present invention, are attained by the subject-matter of the independent claims. Some of the preferred embodiments of the present invention are defined by the subject-matter of the dependent claims.

Surprisingly, it was found that a pharmaceutical composition, and in particular an oral solid dosage form, which comprises macitentan free base form I meets the above-mentioned requirements.

The invention therefore relates to an oral solid dosage form, comprising crystalline macitentan free base characterized by an X-ray powder diffraction pattern showing peak maxima at 2 theta/° values of 11.4±0.2, 13.0±0.2, 16.1±0.2, and 25.4±0.2 when a radiation wavelength of 0.15419 nm is used, and at least one excipient. The X-ray powder diffraction pattern is determined at a temperature of about 22° C.

A further embodiment of the present invention relates to a method for the preparation of a pharmaceutical composition of the present invention, comprising
a) providing Macitentan free base form I;
b) mixing the Macitentan free base form I provided in a) with at least one excipient;
c) preparing the pharmaceutical composition from the mixture obtained in b), optionally including further downstream mixing and processing steps.

A further embodiment of the present invention relates to the use of macitentan free base form I for the preparation of an oral solid dosage form having an increased chemical stability after packaging in a polyethylene film and storing in the dark at 40° C. at a relative humidity of 75% for a period of 14 days, compared with an identically packaged and stored oral solid dosage form comprising, instead of macitentan free base form I, amorphous macitentan free base.

A further embodiment of the present invention relates to a pharmaceutical composition comprising macitentan free base form I, wherein said pharmaceutical composition is packaged in a packaging material having a moisture vapour transmission rate of at least 0.4 g m$^{-2}$ d$^{-1}$ as measured according to standard DIN 53122-1.

A further embodiment of the present invention relates to macitentan free base form I for use in the treatment of pulmonary arterial hypertension in patients in a country having an area with an Af or an Am climate, preferably an Af climate, according to the Köppen-Geiger climate classification.

FIGURE LEGENDS

The drawing: XRPD pattern of Macitentan free base polymorphic form I analyzed according to Reference Example 1. On the x axis, the position [° 2 Theta] (Copper (CuKα)) is shown with explicit values of 10, 20, and 30. On the y axis, the counts are shown with explicit values of 0, 500, and 1000.

DEFINITIONS

Where the term "comprising" is used in the present description and claims, it does not exclude other elements or steps. For the purposes of the present invention, the term "consisting of" is considered to be a preferred embodiment of the term "comprising". If hereinafter a group is defined to comprise at least a certain number of embodiments, this is also to be understood to disclose a group which optionally consists only of these embodiments.

Where an indefinite or definite article is used when referring to a singular noun e.g. "a" or "an", "the", this includes a plural of that noun unless something else is specifically stated.

The term "about" in the context of the present invention denotes an interval of accuracy that the person skilled in the art will understand to still ensure the technical effect of the feature in question. The term typically indicates deviation from the indicated numerical value of ±10%, and preferably ±5%.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The term "oral solid dosage form" as used herein denotes solid preparations (e.g. tablets) for oral administration each containing a single dose of one or more active substances.

In the context of the present invention, the term "dissolution rate" relates to the percentage (weight-%) of macitentan in an oral dosage form which is dissolved after a defined number of minutes if the macitentan-containing oral solid dosage form is subjected to dissolution conditions using an USP 2 apparatus with a stirrer speed of 75 rpm and a test temperature of 37° C. with a dissolution medium of 900 ml of a 0.1 N HCl solution comprising 1% by weight of sodium lauryl sulphate.

In the context of the present invention, the term "macitentan free base form I" or "macitentan free base polymorphic form I" relates to crystalline macitentan free base characterized by an X-ray powder diffraction pattern showing peak maxima at 2 theta/° values of 11.4±0.2, 13.0±0.2, 16.1±0.2, and 25.4±0.2, preferably at 2 theta/° values 11.4±0.2, 13.0±0.2, 16.1±0.2, 18.2±0.2, 18.6±0.2, 22.1±0.2, 25.4±0.2, 26.6±0.2, 28.5±0.2 and of 31.2±0.2 when a radiation having a wavelength of 0.15419 nm is used. The X-ray powder diffraction pattern is determined at a temperature of about 22° C.

In the context of the present invention, the term "chemical stability" means that the sum of all degradation products derived from macitentan is below 2 percent, preferably below 0.5% of the total amount of macitentan after storage at defined conditions. Analysis and detection of degradation products is performed by HPLC.

In the context of the present invention, the term "polymorphic stability" means that macitentan free base form I does not convert to a crystalline form other than macitentan free base form I and does not convert to an amorphous form of macitentan free base, as determined by XRPD.

Detection of other polymorphic forms of macitentan or of amorphous macitentan can be done by XRPD measurements.

In the context of the present invention, the relative content of amorphous Macitentan free base is determined by XRPD. The degree of crystallinity of a given sample can be determined by subjecting the sample XRD and comparing the sample to a range of mixtures of amorphous macitentan with known amounts of crystalline macitentan form I.

The Köppen-Geiger classification is one of the most widely used climate classification systems. It combines average annual and monthly temperatures and precipitation, and the seasonality of precipitation in an area. Examples of countries having an area with an Af climate are Brazil, Indonesia, Mexico, Puerto Rico, Zaire, to name but a few. Examples of countries having an area with an Am climate are Brazil, Indonesia, Mexico, Cuba, the USA, Zaire, India, China, Birma, to name but a few.

Particle size distribution may be described using quantiles, e.g. D5%, D 10%, D50%, D90%, D95% and D98%. As used herein, "particle size distribution" means the cumulative volume size distribution of equivalent spherical diameters as determined by laser diffraction at 1 bar dispersive pressure in a Sympatec Helos equipment.

In the context of the present invention "slightly hygroscopic" means that a tested substance displays a mass increase of at most 2%, but at least 0.2% when tested by the hygroscopicity assay and using the environmental conditions according to 5.11. of the European Pharmacopoeia 7.0.

In the context of the present invention "non-hygroscopic" means that a tested substance displays a mass increase of at most 0.2% when tested by the hygroscopicity assay and using the environmental conditions according to 5.11. of the European Pharmacopoeia 7.0.

DETAILED DESCRIPTION OF THE INVENTION

The present invention illustratively described in the following may suitably be practiced in the absence of any element or elements, limitation or limitations, not specifically disclosed herein.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes.

The present invention relates to a pharmaceutical composition, preferably to an oral solid dosage form, in particular to a tablet, comprising macitentan free base form I, and at least one excipient.

The Oral Solid Dosage Form

Macitentan free base form I can be prepared by processes as described by Bolli et al., J. Med. Chem. 2012, 55, 7849-7861. Further, any other method for the preparation of said crystalline macitentan free base form I is comprised by the present invention provided that said crystalline macitentan free base form I as described above is obtained.

The oral solid dosage form, and preferably the tablet, of the present invention usually contains up to 50% by weight of the macitentan free base form I based on the total weight of the pharmaceutical composition. More preferably, the respective content is from 5% to 20%, such as from 10% to 20%.

The oral solid dosage form, and preferably the tablet, of the present invention exhibit unexpected and advantageous characteristics with respect to their susceptibility to humidity, which characteristics can be observed, e.g., if the oral dosage forms are packaged in a packaging material having a comparatively high moisture vapour transmission rate of at least $0.4$ g m$^{-2}$ d$^{-1}$, preferably of at least $1$ g m$^{-2}$ d$^{-1}$, more preferably of at least $2$ g m$^{-2}$ d$^{-1}$, as measured according to standard DIN 53122-1, and further if the respectively packaged oral dosage forms are stored for a certain period of time, preferably for at least 2 weeks, more preferably for at least 6 months, even more preferably for at least 12 months.

Surprisingly, it is found that after such packaging and storage, the chemical stability and/or polymorphic stability is significantly higher than that of the oral dosage forms prepared from amorphous Macitentan free base, as described in WO 2007/031933, when both oral dosage forms are packaged in the same packaging material and stored for the same time and under the same environmental conditions.

Moreover, it has been found that in the oral solid dosage form, and preferably the tablet, of the invention the crystalline macitentan free base has a more homogeneous distribution than amorphous macitentan free base in the oral dosage forms described in WO 2007/031933, where a tendency for agglomeration of the amorphous drug particles is observed, for example already during the formulation process.

For optimal homogeneity of the drug particle distribution in the oral solid dosage form, and preferably the tablet, macitentan free base form I is provided as a composition of macitentan free base form I crystals with a defined particle size. Thus, in one embodiment, the composition of macitentan free base form I crystals to be used for the preparation of the oral solid dosage form, and in particular the tablet, of the present invention has a particle size distribution having a D98% of at most 680 µm and a D5% of at least 0.5 µm, optionally also having a D50% of from 3 µm to 250 µm, in particular of from 15 µm to 150 µm. A preferred particle size distribution corresponds to: D98%: 650-680 µm; D50%: 230-250 µm; and D5%: 40-60 µm. Another preferred particle size distribution corresponds to: D98%: 370-390; d50%: 100-120 µm; D5%: 5-15 µm. Another preferred particle size distribution corresponds to: D98%: 100-125 µm; D50%: 15-25 µm; and D5%: 1-3 µm. Another preferred particle size distribution corresponds to: D98%: 50-70 µm; D50%: 3-7 µm; and D5%: 0.5-2.

These particle size distributions strike a beneficial balance between processability during formulation—crystals which are too small may stick to the plunger in a tableting machine—on the one hand and dissolution rate on the other—if the crystals are too large this may gradually compromise the bioavailability of macitentan.

According to the present invention, oral solid dosage form, and preferably the tablet, contains at most 20% by weight, preferably at most 15% by weight, more preferably at most 10% by weight, more preferably at most 5% by weight, more preferably at most 2% by weight of amorphous macitentan free base. Most preferably they don't contain detectable amounts of amorphous macitentan free base.

The oral solid dosage form, and preferably the tablet, of the present invention comprises at least one excipient. Generally, there are no specific restrictions concerning the chemical nature of these excipients provided that the excipient or mixture of excipients comprised in the oral solid dosage form is/are pharmaceutically acceptable. A pharmaceutically acceptable excipient is an excipient which is relatively non-toxic and innocuous to a patient at concentrations consistent with effective activity of the crystalline macitentan free base form I so that any side effects ascribable to the excipient do not vitiate the beneficial effects of the crystalline macitentan free base form I. Therefore, according to the present invention, excipients are, for example, disintegrants, binders, lubricants, fillers, plasticizers, surfactants and wetting agents, film-forming agents and coating materials, sweeteners, flavoring agents, and coloring agents such as example pigments. Other excipients known in the field of pharmaceutical compositions may also be used.

Suitable disintegrants according to the present invention include, but are not limited to, carboxymethylcellulose calcium, carboxymethylcellulose sodium, croscarmellose (crosslinked carboxymethylcellulose) sodium, cross-linked polyvinylpyrrolidone, crospovidone (cross-linked povidone, a synthetic cross-linked homopolymer of N-vinyl-2-pyrrolidone), alginic acid, microcrystalline cellulose (such as refined wood pulp derived from alpha cellulose), hydroxypropyl cellulose, low substituted hydroxypropyl cellulose, polacrillin potassium, sodium alginate, sodium starch glycolate, partially hydrolysed starch, sodium carboxymethyl starch, and starch.

Suitable binders according to the present invention include, but are not limited to, hydroxypropyl cellulose, hypromellose (hydroxypropyl methylcellulose, HPMC), microcrystalline cellulose, acacia, alginic acid, carboxymethylcellulose, ethylcellulose, methylcellulose, hydroxyethylcellulose, ethylhydroxyethylcellulose, polyvinyl alcohol, polyacrylates, carboxymethylcellulose calcium, carboxymethylcellulose sodium, compressible sugar, ethylcellulose, gelatin, liquid glucose, methylcellulose, polyvinyl pyrrolidone and pregelatinized starch.

Suitable lubricants according to the present invention include, but are not limited to, calcium stearate, magnesium stearate, mineral oil, stearic acid, fumaric acid, sodium stearylfumarate, zinc stearate and polyethylene glycol.

Suitable fillers according to the present invention include, but are not limited to, dibasic calcium phosphate, kaolin, microcrystalline cellulose, silicated microcrystalline cellulose, dicalcium phosphate, tricalcium phosphate, magnesium trisilicate, lactose such as example the anhydrous form or the hydrate form such as the monohydrate form, sugars such as dextrose, maltose, saccharose, glucose, fructose or maltodextrine, sugar alcohols such as mannitol, maltitol, sorbitol, xylitol, powdered cellulose, precipitated calcium carbonate, sodium carbonate, sodium phosphate and starch. Fillers which are slightly hygroscopic or non-hygroscopic are preferred, with non-hygroscopic fillers being particularly preferred, in particular when the dosage form is to be used for tropical countries.

Suitable surfactants and wetting agents according to the present invention include, but are not limited to, heptadecaethylene oxycetanol, lecithins, sorbitol monooleate, polyoxyethylene sorbitol monooleate, polyoxyethylene stearate, polyoxyethylen sorbitan monolaurate, benzalkonium chloride, nonoxynol 10, oxtoxynol 9, polysorbates, for example polysorbate 20, polysorbate 40, polysorbate 60 or polysorbate 80, sorbitan monopalmitate, sodium salts of fatty alcoholsulfates such as sodium lauryl sulfate, sodium dodecylsulfate, sodium salts of sulfosuccinates such as sodium dioctylsulfosuccinate, partially esters of fatty acids with alcohols such as glycerine monostearate, partially esters of fatty acids with sorbitans such as sorbitan monolaurate, partially esters of fatty acids with polyhydroxyethylene sorbitans such as polyethyleneglycol sorbitan monolaurate, -monostearate or -monooleate, ethers of fatty alcohols with polyhydroxyethylene, esters of fatty acids with polyhydroxyethylene, copolymers of ethylenoxide and propylenoxide (Pluronic®) and ethoxylated triglycerides.

Suitable film-forming agents and coating materials according to the present invention include, but are not limited to, liquid glucose, hydroxyethyl cellulose, hydroxypropyl cellulose, hydroxypropyl methylcellulose (hypromellose, HPMC), methylcellulose, ethylcellulose, cellulose acetate phthalate, shellac, polyvinylpyrrolidone, copolymers of vinylpyrrolidone and vinylacetate such as Kollidon® VA64 BASF, copolymers of acrylic and/or methacrylic acid esters with trimethylammoniummethylacrylate, copolymers of dimethylaminomethacrylic acid and neutral methacrylic acid esters, polymers of methacrylic acid or methacrylic acid esters, copolymers of acrylic acid ethylester and methacrylic acid methyl ester, and copolymers of acrylic acid and acrylic acid methylester.

Suitable plasticizers according to the present invention include, but are not limited to, polyethylene glycol, diethyl phthalate and glycerol. Preference is given to polyethylene glycol.

Suitable coloring agents according to the present invention include, but are not limited to, pigments, inorganic pigments, FD&C Red No. 3, FD&C Red No. 20, FD&C Yellow No. 6, FD&C Blue No. 2, D&C Green No. 5, D&C Orange No. 5, D&C Red No. 8, caramel, ferric oxide red, ferric oxide yellow and titanium dioxide.

Suitable further commonly used excipients which may be used according to the present invention include, but are not limited to, acidifying agents such as acetic acid, citric acid, fumaric acid, hydrochloric acid and nitric acid; alkalizing agents such as ammonia solution, ammonium carbonate, diethanolamine, monoethanolamine, potassium hydroxide, sodium borate, sodium carbonate, sodium hydroxide, triethanolamine and trolamine; adsorbents such as powdered cellulose and activated charcoal; stabilizers and antioxidants such as ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate and sodium metabisulfite; binding materials such as block polymers, natural and synthetic rubber, polyacrylates, polyurethanes, silicones, polysiloxanes and styrene-butadiene copolymers; buffering agents such as potassium metaphosphate, dipotassium phosphate, sodium acetate, sodium citrate anhydrous and sodium citrate hydrates; encapsulating agents such as gelatin, starch and cellulose derivates; flavorants, masking agents and odors such as anise oil, cinnamon oil, cocoa, menthol, orange oil, peppermint oil and vanillin; humectants such as glycerol, propylene glycol and sorbitol; sweeteners such as aspartame, dextrose, glycerol, mannitol, propylene glycol, saccharin sodium, sorbitol and sucrose; anti-adherents such as magnesium stearate and talc; direct compression excipients such as dibasic calcium phosphate, lactose and microcrystalline cellulose; tablet polishing agents such as carnauba wax and white wax.

The skilled person will appreciate that depending upon formulation context and concentration a particular excipient can fulfill various and sometimes even different functions. For example, microcrystalline cellulose is a particular hydrolyzed cellulose, which can be used as a filler, binder and/or disintegrating material in tablet production, dependent on formulation context and concentration. Reference is made to the literature on pharmaceutical excipients and pharmaceutical formulation, such as Fiedler Encyclopedia of Excipients for Pharmaceuticals, Cosmetics and Related Areas. Wissenschaftliche Verlagsgesellschaft Stuttgart, 2013, Bauer, Frömming and Führer, "Lehrbuch der Pharmazeutischen Technologie" Wissenschaftliche Verlagsgesellschaft Stuttgart, 9. Auflage (2012) or, with a particular focus on tablet production, Augsburger and Stephen, Pharmaceutical Dosage Forms: Tablets, Third Edition, Volume 2, Informa Healthcare (2008). The skilled person will therefore appreciate that terms like "disintegrant", "binder", "lubricant", "filler", "plasticizer", "surfactant", "wetting agent", "film-forming agent", "coating material", "sweetener", "flavoring agent" and "coloring agent" are primarily functional definitions and that the structural characterization provided above are given so as to more easily allow identification of suitable excipients.

The oral solid dosage form of the present invention is preferably a compressed or a non-compressed dosage form. Preferably, the oral solid dosage form of the present invention is a granule, a capsule, for example a capsule filled with granules, a sachet, a pellet, a dragee, a lozenge, a troche, a pastille, or a tablet, such as an uncoated tablet, a coated tablet, an effervescent tablet, a soluble tablet, a dispersible tablet, an orodispersible tablet, a tablet for use in the mouth, a chewable tablet or an extrudate. Preferably, the longest dimension of an oval tablet or of a capsule is at most 25 mm; as to a round tablet should, a preferred diameter is at most 13 mm.

Tablet

According to a preferred embodiment of the present invention, the oral solid dosage form is a compressed dosage form. More preferably, the oral solid dosage form is a tablet. Tablets can be prepared by compressing uniform volumes of particles or particle aggregates, preferably produced by granulation methods. In the manufacture of such tablets, means are taken to ensure that they possess a suitable mechanical strength to avoid crumbling or breaking on handling or subsequent processing. The process of providing tablets is well known to the skilled person.

According to this embodiment, the tablet of the present invention preferably comprises at least one excipient selected from the group consisting of fillers, disintegrants, lubricants, and surfactants. More preferably, the tablet of the present invention comprises at least one filler and at least one disintegrant and at least one lubricant and at least one surfactant. Even more preferably, the tablet comprises at least one filler, preferably lactose or lactose monohydrate, in an amount of from 10% to 90%, preferably from 30% to 80%, more preferably from 50% to 75%, at least one disintegrant, preferably microcrystalline cellulose, in an amount of from 2% to 10%, preferably from 4% to 8% by weight, at least one binder, preferably polyvinylpyrrolidone, in an amount of from 0.5% to 8%, preferably from 1% to 5% by weight, at least one lubricant, preferably magnesium stearate, in an amount of from 0.1 to 1.0, preferably from 0.2 to 0.8% by weight, and at least one surfactant, preferably Polyoxyethylen-(20)-sorbitanmonooleat, in an amount of from 0.1% to 0.5%, preferably from 0.15% to 0.3% by weight, in each case relative to the total weight of the tablet.

The tablet of the present invention usually contains up to 50% by weight of the macitentan free base form I based on the total weight of the pharmaceutical composition. More preferably, the respective content is from 5% to 20%, such as from 10% to 20%.

A preferred dissolution rate of the tablet according to this embodiment of the present invention is at least 50% in 15 min. Preferably, the dissolution rate is at least 90% in 50 min, more preferably at least 50% in 15 min and at least 90% in 50 min, and in particular at least 80% in 15 min and at least 90% in 40 min.

According to an especially preferred embodiment, the present invention relates to an tablet comprising macitentan free base form I in an amount of from 2% to 10% by weight, lactose in an amount of from 50% to 75% by weight, polyvinylpyrrolidone in an amount of from 2% to 5% by weight, microcrystalline cellulose in an amount of from 4% to 8% by weight, sodium starch glycolate in an amount of from 1% to 3% by weight, magnesium stearate in an amount of from 0.2 to 0.8% by weight, in each case relative to the total weight of the tablet.

As to this especially preferred embodiment of the present invention, it was found that the chemical stability of macitentan in said tablet is significantly higher after 30 days storage at 40° C./75% r.h. than in equivalent tablets where amorphous macitentan free base was used instead of macitentan free base form I.

Method for the Preparation of the Oral Solid Dosage Form

Generally, there are no specific restrictions concerning the method for the preparation of the oral solid dosage form according to the present invention provided that the oral dosage form is obtained.

Preferably, the present invention relates to a method for the preparation of an oral solid dosage form, preferably the tablet as discussed above, said method comprising
a) providing macitentan free base form I;
b) mixing the macitentan free base form I provided in a) with at least one excipient;
c) preparing the oral solid dosage form based on the mixture obtained in b).

The skilled person will appreciate that step c) can comprise further mixing and processing steps so as to arrive at the desired oral solid dosage form, e.g. the tablet, of the invention.

Concerning possible excipients, reference is made to the excipients described above. Most preferably, the macitentan free base form I and the at least one excipient are employed in amounts which allow for obtaining the oral solid dosage form, e.g. the tablet, as described above.

Preferably, the oral solid dosage forms, e.g. the tablet, are/is prepared by granulation according to which method the macitentan free base form I provided in a) and at least one excipient are granulated to obtain a granulate, optionally followed by blending the obtained granulate with at least one further excipient. The granulate, or optionally the blended granulate, can be optionally coated with at least one further excipient.

Granulation of the macitentan free base form I provided in a) and the at least one excipient is preferably carried out as a wet-granulation process. According to such wet-granulation process, the macitentan free base form I provided in a) and the at least one excipient are preferably admixed with a suitable granulation liquid, preferably water, and granulated. Prior to mixing, the water can be admixed with at least one excipient; in this case, it is preferred to admix at least one of the surfactants with the water, if such a surfactant is employed at all. Further excipients, such as fillers, disintegrants and surfactants may be present during the granulation step.

Granulation can be performed according to all conceivable methods. For example, in case the oral dosage form is to be prepared in large-scale numbers, a high-shear mixer can be employed. The damp mass obtained can then be passed through a sieve such as an oscillating sieve with, for example, a 1-4 mm mesh size. In case the oral dosage form is to be prepared in small-scale numbers, mixing can be performed manually such as with a mortar and a pistil, and the granulation can be performed by making use of a suitably-sized sieve such as a prescription sieve with, for example, a 1-4 mm mesh size. The granulates obtained are preferably suitably dried, such as in a fluidized-bed dryer tray dryer, at preferred temperatures in the range of from 50 to 120° C., preferably from 50 to 70° C. until the residual moisture content of the oral solid dosage form is preferably at most 3% by weight, more preferably at most 2% by weight, more preferably at most 1% by weight. Optionally after drying, the dried granules can be sieved again.

After the granulation process, the preferably dried granulates can be milled and optionally blended with at least one further excipient, preferably with a disintegrant, more preferably sodium starch glycolate, before a lubricant, such as magnesium stearate is added and the resulting mixture is used in a further blending step. Any conceivable device can be employed for such blending process. A suitable device is, for example, a tumbler blender, and typical tumbling times are with a range of from 5 to 10 minutes.

The preferably dried granulates, optionally blended with at least one excipient, are then optionally compacted, for example compressed, to give the optionally blended granulate a desired shape, such as the shape of a pastille, a pellet, or preferably a tablet.

Therefore, the present invention relates to the method above, wherein in c), the oral solid dosage form based on the mixture obtained in b) is prepared by
c1) granulating, preferably wet-granulating the mixture obtained in b), wherein as granulation liquid, water is employed optionally comprising at least one excipient;
c2) blending the granulate obtained in c1) with at least one excipient;
c3) optionally compressing the optionally blended granulate.

Subsequently, the optionally blended and/or optionally compacted, preferably compressed granulate can be suitably coated such as film-coated with at least one excipient. This at least one excipient is preferably selected from the group consisting of film-forming agents, plasticizers and coloring agents. Suitable film-forming agents, plasticizers and coloring agents are described above. Therefore, the present invention also relates to a process as described above, additionally comprising d) coating the compacted, preferably compressed granulate with at least one excipient.

The oral solid dosage form, e.g. the tablet, of the present invention comprising the macitentan free base form I is preferably used in the treatment of pulmonary arterial hypertension.

As discussed above, the oral solid dosage form, e.g. the tablet, of the present invention, when compared to the known dosage form comprising the amorphous macitentan free base, is characterized by a lower susceptibility to humidity. It has thus better properties when stored in a humid environment for a prolonged period of time in comparison to solid dosage forms, e.g. tablets, containing amorphous macitentan free base. Therefore, the oral solid dosage form, e.g. the tablet, of the present invention is particularly useful if it is to be employed in a country having a tropical climate. In this case it is not necessary to package the oral solid dosage form, e.g. the tablet, of the invention in aluminum blisters. Therefore, this advantageous characteristic of the oral dosage form, e.g. the tablet, according to the present invention allows for the use of convenient packaging material. Preferred packaging materials have a vapour transmission rate of at least 0.4 g m$^{-2}$ d$^{-1}$, preferably of at least 1 g m$^{-2}$ d$^{-1}$, more preferably of at least 2 g m$^{-2}$ d$^{-1}$, as measured according to standard DIN 53122-1. Some preferred packaging materials are polyethylene, polypropylene, polyethylene terephthalate, polystyrene, polyvinyl chloride and polyvinylidene chloride. Other preferred packaging materials are polypropylene foil and polyvinyl chloride foil.

Therefore, the present invention also relates to the oral solid dosage form, e.g. the tablet, of the present invention for use in the treatment of pulmonary arterial hypertension, wherein the oral dosage form, e.g. the tablet, is to be administered to patients in a country having an area with an Af or an Am climate, preferably an Af climate, according to the Köppen-Geiger climate classification. Moreover the present invention relates to the oral solid dosage form, e.g. the tablet, of the present invention for use in the treatment of pulmonary arterial hypertension, wherein the oral dosage form, e.g. the tablet, is to be administered to patients in a country having an area with an Af or an Am climate, preferably an Af climate, according to the Köppen-Geiger climate classification, and wherein the oral dosage form is packaged in a packaging material having a vapour transmission rate of at least 0.4 g m$^{-2}$ d$^{-1}$, preferably of at least 1 g m$^{-2}$ d$^{-1}$, more preferably of at least 2 g m$^{-2}$ d$^{-1}$, as measured according to standard DIN 53122-1

The present invention also relates to macitentan free base form I for use in the treatment of pulmonary arterial hypertension, wherein the oral dosage form, e.g. the tablet, is to be administered to patients in a country having an area with an Af or an Am climate, preferably an Af climate, according to the Köppen-Geiger climate classification. The present invention also relates to macitentan free base form I for the preparation of a dosage form, which dosage form is packaged in a packaging material having a vapour transmission rate of at least 0.4 g m$^{-2}$ d$^{-1}$, preferably of at least 1 g m$^{-2}$ d$^{-1}$, more preferably of at least 2 g m$^{-2}$ d$^{-1}$, as measured according to standard DIN 53122-1. Preferred dosage forms in this embodiment are oral solid dosage form, e.g. tablets.

Further, the present invention relates to the use of macitentan free base form I for the preparation of an oral solid dosage form, e.g. a tablet, having increased chemical stability after packaging in a polypropylene film and storage in the dark at 40° C. at a relative humidity of 75% for a period of at least 14 days, compared to an identically packaged and stored oral solid dosage form comprising, instead of macitentan free base form I, amorphous macitentan free base.

Pharmaceutical Composition

The above-described advantage of macitentan free base form I with regard to an improved, i.e. lower susceptibility to humidity compared to amorphous macitentan is not restricted to the above-described oral solid dosage forms.

Therefore, the present invention generally also relates to a pharmaceutical composition comprising crystalline macitentan free base form I, wherein said pharmaceutical composition is packaged in a packaging material having a moisture vapour transmission rate of at least 0.4 g m$^{-2}$ d$^{-1}$ as measured according to standard DIN 53122-1, said packaging material preferably being made from polyethylene, polypropylene, polyvinylidene chloride and/or polyvinylchloride, for example packaging material made from a combination of polyvinylchloride and polyvinylidenechloride (PVC/PVDC), with polypropylene and polyvinylchloride being preferred.

While the present invention has been described with respect to some preferred embodiments, this is in no way to limit the scope of the invention. The person skilled in the art is clearly aware of further embodiments and variations to the above-described embodiments which are still within the scope of the present invention.

EXAMPLES

Analytical Methods
X-Ray Powder Diffraction
XRPD analysis was carried out on a Siemens D5000, scanning the samples between 3 and 30° 2-theta or between 3 and 50° 2-theta. The sample was loaded into a Siemens D5000 diffractometer running in reflection mode and analysed, using the following experimental conditions.
Raw Data Origin Siemens-Binary V2 (.RAW)
Start Position [° 2Th.] 3.0000
End Position [° 2Th.] 30 or 50
Step Size [° 2Th.] 0.0200
Scan Step Time [s] 1
Scan Type Continuous
Offset [° 2Th.] 0.0000
Divergence Slit Type Fixed
Divergence Slit Size [°] 2.0000
Specimen Length [mm] various
Receiving Slit Size [mm] 0.2000
Measurement Temperature [° C.] 20.00
Anode Material Cu
K-Alpha1/2 [Å] 1.5419
K-A2/K-A1 Ratio 0.50000 (nominal)
Generator Settings 40 mA, 40 kV
Diffractometer Type d5000
Diffractometer Number 0
Goniometer Radius [mm] 217.50
Incident Beam Monochromator No
Diffracted Beam Monochromator (Graphite)
Spinning No (unless otherwise stated)
b) Dynamic Vapour Sorption (DVS)

Approximately 10-20 mg of sample was placed into a mesh vapour sorption balance pan and loaded into a DVS-1 dynamic vapour sorption balance by Surface Measurement Systems.

The sample was subjected to a ramping profile from 0 to 90% relative humidity (RH) at 10% increments, maintaining the sample at each step until a stable weight had been achieved (99.5% step completion). After completion of the sorption cycle, the sample was dried using the same procedure, all the way down to 0% RH. The weight change during the sorption/desorption cycles were plotted, allowing for the hygroscopic nature of the sample to be determined.

c) Dissolution Testing

Detection of dissolved Macitentan in dissolution experiments is as described on pages 32-34 of WO 2007/031933 A2. The same HPLC parameters as described on the top of page 33 are used, the same protocol as described starting in line 4 on page 33 and ending at the bottom of page 34, is used.

Reference Example: Characterization of Macitentan Free Base Form I a) Characterization of Polymorph I Crystalline Macitentan free base of polymorphic form I was prepared according to Bolli et al., J. Med. Chem. 2012, 55, 7849-7861, by crystallization from methanol. It was analyzed by X-ray diffraction as described above. An X-ray powder diffraction pattern was obtained which is shown in the drawing and which is also characterized by the following Table 1.

TABLE 1

X-ray powder diffraction pattern polymorph form I

| Pos. [°2θ] | Height [counts] | Rel. Int. [%] |
|---|---|---|
| 6.5411 | 52.82 | 4.82 |
| 8.0550 | 103.60 | 9.45 |
| 11.4302 | 557.08 | 50.83 |
| 13.0565 | 552.60 | 50.42 |
| 13.3095 | 119.10 | 10.87 |
| 13.9794 | 96.00 | 8.76 |
| 14.3080 | 132.73 | 12.11 |
| 16.0866 | 745.90 | 68.06 |
| 17.2439 | 191.01 | 17.43 |
| 18.0274 | 322.53 | 29.43 |
| 18.2011 | 598.77 | 54.63 |
| 18.5968 | 575.41 | 52.50 |
| 19.6344 | 122.04 | 11.14 |
| 20.1159 | 309.49 | 28.24 |
| 21.3143 | 405.13 | 36.97 |
| 22.0680 | 438.75 | 40.03 |
| 22.7138 | 166.95 | 15.23 |
| 22.9664 | 262.15 | 23.92 |
| 23.2869 | 317.95 | 29.01 |
| 23.4412 | 403.92 | 36.85 |
| 24.6039 | 72.82 | 6.64 |
| 25.3825 | 1095.98 | 100.00 |
| 25.6312 | 207.87 | 18.97 |
| 26.0865 | 171.10 | 15.61 |
| 26.6255 | 402.40 | 36.72 |
| 26.7549 | 285.25 | 26.03 |
| 27.6769 | 137.97 | 12.59 |
| 28.2250 | 337.36 | 30.78 |
| 28.5431 | 605.05 | 55.21 |
| 29.0912 | 47.61 | 4.34 |
| 29.7400 | 60.67 | 5.54 |
| 29.9800 | 41.49 | 3.79 |
| 31.2104 | 676.23 | 61.70 |
| 31.7596 | 99.87 | 9.11 |
| 32.4598 | 68.05 | 6.21 |

TABLE 1-continued

X-ray powder diffraction pattern polymorph form I

| Pos. [°2θ] | Height [counts] | Rel. Int. [%] |
|---|---|---|
| 32.9885 | 196.91 | 17.97 |
| 33.7344 | 72.14 | 6.58 |
| 34.3275 | 138.27 | 12.62 |
| 34.5516 | 91.22 | 8.32 |
| 35.5443 | 72.10 | 6.58 |
| 36.5057 | 49.39 | 4.51 |
| 36.8399 | 65.36 | 5.96 |
| 37.3586 | 102.83 | 9.38 |
| 37.6373 | 168.83 | 15.40 |
| 37.8719 | 116.78 | 10.66 |
| 38.4582 | 108.00 | 9.85 |
| 38.9354 | 14.38 | 1.31 |
| 39.6074 | 61.04 | 5.57 |
| 39.8105 | 125.50 | 11.45 |
| 40.9580 | 25.94 | 2.37 |
| 41.6265 | 40.86 | 3.73 |
| 42.2388 | 165.91 | 15.14 |
| 43.1587 | 144.48 | 13.18 |
| 43.8377 | 75.12 | 6.85 |
| 44.1984 | 146.16 | 13.34 |
| 44.8763 | 126.14 | 11.51 |
| 45.5906 | 58.37 | 5.33 |
| 46.8113 | 317.61 | 28.98 |
| 46.9662 | 165.65 | 15.11 |
| 47.7812 | 33.29 | 3.04 |
| 48.5246 | 47.01 | 4.29 |
| 48.8682 | 88.65 | 8.09 |
| 49.6000 | 60.41 | 5.51 |

Example 1

70 mg tablets were prepared by a wet granulation process. Tablets prepared from 10 mg Macitentan free base form I were compared with tablets prepared from 10 mg amorphous Macitentan free base.

The tablet composition for a unit dose is provided below: Intragranular components were 39.0 mg Pharmatose 200M, 3.3 mg Avicel PH101, 2.2 mg Povidone K30, 1.4 mg sodium starch glycolate, 0.14 mg Tween 80V, water q.s.; Extragranular components were 12.25 mg Avicel PH101, 1.45 mg sodium starch glycolate and 0.30 mg magnesium stearate.

Tablets were prepared essentially as described in WO2007/031933 A2 on page 18, briefly by mixing the intragranular components (without Tween) in a blender, then granulating with Tween/water, drying the granules, sieving the granules through a 500 μm sieve, adding the extragranular components without Mg-Stearate and blending, then adding the magnesium stearate and blending, sieving, blending again and compressing into tablets having a hardness of from 3 kp to 9 kp. They were then coated with opadry AMB using the coating methodology described on page 19, line 4 to page 20, line 5 of WO 2007/031933 A2.

Example 2

The coated tablets prepared from macitentan free base form I were compared with coated tablets prepared from amorphous Macitentan free base.

After 4 weeks storage at 25° C. and at 60% relative humidity the tablets prepared from macitentan free base form I were significantly better than the tablets prepared from amorphous Macitentan free base with regard to chemical stability.

The tablets prepared from macitentan free base form I were also significantly better with regard to polymorphic stability. XRPD patterns obtained from freshly prepared tablets (from example 1) and from stored tablets (from example 2) were virtually identical, demonstrating a very high degree of polymorphic stability of form I in the context of the tablets.

In contrast thereto, the tablets prepared from amorphous macitentan free base changed over time upon storage. XRPD patterns obtained from freshly prepared tablets (from example 1) and from stored tablets (from example 2) showed visible differences. These differences were indicative that a solid form transformation occurred for at least part of the starting material, the amorphous macitentan free base, upon prolonged storage. Thus—in comparison to the tablets prepared from macitentan free base form I—the amorphous form of macitentan free base was not as stable upon prolonged storage in the context of the tablets.

Example 3

The coated tablets are packaged in polypropylene blisters. After 4 weeks storage at 40° C. and at 70% relative humidity the tablets prepared from macitentan free base form I are significantly better than the tablets prepared from amorphous Macitentan free base with regard to chemical and polymorphic stability. When tested in the dissolution assay, the tablets show a preferred dissolution rate.

Example 4

Compositions of macitentan free base form I with varying particle size distribution are prepared my milling. Particle size distribution is determined by measuring the cumulative volume size distribution of equivalent spherical diameters as determined by laser diffraction at 1 bar dispersive pressure in a Sympatec Helos equipment. Coated tablets are prepared as described in example 1 from the milled crystalline macitentan free base form 1 compositions, namely A) a composition having a particle size distribution of: D98%: 650-680 μm; D50%: 230-250 μm; and D5%: 40-60 μm;
B) D98%: 370-390; d50%: 100-120 μm; D5%: 5-15 μm;
C) D98%: 100-125 μm; D50%: 15-25 μm; and D5%: 1-3 μm; and
D): D98%: 50-70 μm; D50%: 3-7 μm; and D5%: 0.5-2.

After 4 weeks storage at 40° C. and at 70% relative humidity the dissolution rate of the tablets is determined.

The invention claimed is:

1. A packaged pharmaceutical composition comprising:
a pharmaceutical composition comprising crystalline Macitentan free base having an X-ray powder diffraction pattern showing peak maxima at 2 theta/° values of 11.4±0.2, 13.0±0.2, 16.1±0.2, and 25.4±0.2 when a radiation wavelength of 1.5419 Å is used; and at least one excipient; and comprising at most 5% by weight of amorphous Macitentan free base,
wherein said pharmaceutical composition is an oral solid dosage form packaged in a packaging material having a moisture vapor transmission rate of at least 0.4 g m−2 d−1 as measured according to standard DIN 53122-1, wherein when storing the packaged pharmaceutical composition in the dark at 40° C. at a relative humidity of 75% for a period of at least 14 days, the pharmaceutical composition has increased chemical stability when compared to an identically prepared, packaged and stored solid dosage form pharmaceutical composition having only amorphous Macitentan free base as the active agent.

2. The packaged pharmaceutical composition according to claim 1, comprising at most 1% by weight of amorphous Macitentan free base.

3. The packaged pharmaceutical composition according to claim 1, being a compressed dosage form.

4. The packaged pharmaceutical composition according to claim 1, being a tablet.

5. The packaged pharmaceutical composition according to claim 1, being an immediate release tablet.

6. The packaged pharmaceutical composition according to claim 1, comprising at least one filler, at least one desintegrant, at least one binder, at least one lubricant, and at least one surfactant.

7. The packaged pharmaceutical composition according to claim 1, wherein the crystalline Macitentan free base has a particle size distribution having a D98% of at most 680 μm and a D5% of at least 0.5 μm.

8. The packaged pharmaceutical composition according to claim 1, wherein the crystalline Macitentan free base has a particle size distribution having a D50% of from 3 μm to 250 μm.

9. The packaged pharmaceutical composition according to claim 1, wherein the crystalline Macitentan free base has a particle size distribution having a D50% of from 15 μm to 150 μm.

10. The packaged pharmaceutical composition according to claim 1, wherein the oral solid dosage form is to be administered to patients in a country having an area with an Af or an Am climate according to the Köppen-Geiger climate classification.

11. The packaged pharmaceutical composition according to claim 1, wherein said packaging material comprising polypropylene, polyvinylidenchloride and/or polyvinylchloride.

12. The packaged pharmaceutical composition according to claim 1, for use in the treatment of pulmonary arterial hypertension in patients in a country having an area with an Af or an Am climate according to the Köppen-Geiger climate classification.

13. A method for the preparation of a packaged pharmaceutical composition according to claim 1 comprising:
a) providing crystalline Macitentan free base according to claim 1;
b) mixing the crystalline Macitentan free base provided in a) with at least one excipient;
c) preparing the pharmaceutical composition from the mixture obtained in b); and
d) packaging the pharmaceutical composition in the packaging material.

14. The method according to claim 13, further comprising forming the pharmaceutical composition into an oral dosage form.

15. The method according to claim 13, wherein the crystalline Macitentan free base of step a) is a composition of crystals of crystalline Macitentan free base according to claim 1 which has a particle size distribution having a D98% of at most 680 μm and a D5% of at least 0.5 μm.

16. The method according to claim 13, wherein the crystalline Macitentan free base of step a) is a composition of Macitentan free base form I crystals which have a particle size distribution having a D50% of from 3 μm to 250 μm.

17. The method according to claim 13, wherein the crystalline Macitentan free base of step a) is a composition of Macitentan free base form I crystals which have a particle size distribution having a D50% of from 15 μm to 150 μm.

18. A method of making a packaged oral solid dosage form comprising:

forming the oral solid dosage from the crystalline Macitentan free base according to claim 1; and packaging the oral solid dosage form, wherein when the oral solid dosage form is packaged in a polypropylene film.

19. The packaged pharmaceutical composition according to claim 1, which is in the form of a tablet comprising the crystalline Macitentan free base in an amount of from 2% to 10% by weight, lactose in an amount of from 50% to 75% by weight, polyvinylpyrrolidone in an amount of from 2% to 5% by weight, microcrystalline cellulose in an amount of from 4% to 8% by weight, sodium starch glycolate in an amount of from 1% to 3% by weight, magnesium stearate in an amount of from 0.2 to 0.8% by weight, in each case relative to the total weight of the tablet.

20. The packaged pharmaceutical composition according to claim 1, wherein the packaging material comprises a polypropylene film.

21. The packaged pharmaceutical composition according to claim 1, wherein the oral solid dosage form is to be administered to patients in a country having an area with an Af climate according to the Köppen-Geiger climate classification.

22. A packaged oral pharmaceutical composition comprising:

a coated tablet comprising a compressed pharmaceutical composition in an oral solid dosage form and a coating covering the compressed pharmaceutical composition, the pharmaceutical composition comprising crystalline Macitentan free base having an X-ray powder diffraction pattern showing peak maxima at 2 theta/° values of 11.4±0.2, 13.0±0.2, 16.1±0.2, and 25.4±0.2 when a radiation wavelength of 1.5419 Å is used, the crystalline Macitentan free base has a particle size distribution having a D98% of at most 680 μm and a D5% of at least 0.5 μm; at most 5% by weight of amorphous Macitentan free base; and at least one excipient, wherein the coated tablet is packaged in a packaging material having a moisture vapour transmission rate of at least 0.4 g m$^{-2}$ d$^{-1}$ as measured according to standard DIN 53122-1.

* * * * *